(12) United States Patent
Brem

(10) Patent No.: US 7,919,478 B2
(45) Date of Patent: Apr. 5, 2011

(54) METHOD FOR TREATING DIABETIC ULCERS WITH VECTORS ENCODING VEGF

(75) Inventor: Harold Brem, Bronx, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 12/017,688

(22) Filed: Jan. 22, 2008

(65) Prior Publication Data
US 2008/0175820 A1 Jul. 24, 2008

Related U.S. Application Data

(63) Continuation of application No. 10/388,825, filed on Mar. 12, 2003, now abandoned.

(60) Provisional application No. 60/363,584, filed on Mar. 12, 2002.

(51) Int. Cl.
*A61K 48/00* (2006.01)
*A01N 63/00* (2006.01)
*C07H 21/04* (2006.01)

(52) U.S. Cl. ............... 514/44 R; 424/93.2; 536/23.5

(58) Field of Classification Search .................. None
See application file for complete search history.

(56) References Cited

U.S. PATENT DOCUMENTS

| | | | |
|---|---|---|---|
| 5,194,596 A | 3/1993 | Tischer et al. | |
| 5,879,713 A | 3/1999 | Roth et al. | |
| 6,040,157 A | 3/2000 | Hu et al. | |
| 6,329,348 B1 * | 12/2001 | Crystal et al. | 514/44 |
| 6,596,296 B1 * | 7/2003 | Nelson et al. | 424/426 |
| 6,821,512 B1 * | 11/2004 | Gao et al. | 424/93.2 |
| 7,223,740 B2 * | 5/2007 | Visser et al. | 514/44 |

FOREIGN PATENT DOCUMENTS

WO  WO 00/54745  9/2000

OTHER PUBLICATIONS

Kaya, et al. (2001) Sarcoma, 5(4): 197-202.*
Bennett, et al. (2003) British Journal of Surgery, 90: 133-146.*
Abraham, et al., "Psoriasis, necrobiosis lipoidica, granuloma annnulare, vitiligo and skin infections in the same diabetic patient," *J. Dermatol.* 17(7): 440-447 (1990).
Acsadi, et al., "Human dystrophin expression in mdx mice after intramuscular injection of DNA construct," *Nature* 352(6338): 815-818 (1991).
Albertson, et al., "PDGF and FGF reverse the healing impairment in protein-malnourished diabetic mice," *Surgery* 114(2): 368-373 (1993).
Altavilla, et al., "Inhibition of lipid peroxidation restores impaired vascular endothelial growth factor expression and stimulates wound healing and angiogenesis in the genetically diabetic mouse," *Diabetes* 50(3): 667-674 (2001).
Arbiser, "Angiogenesis and the skin: a primer," *J. Am. Acad. Dermatol.* 34(3): 486-497 (1996).
Arnold & West, "Angiogenesis in wound healing," *Pharmacol. Ther.* 52(3): 407-422 (1991).
Banai, et al., "Angiogenic-induced enhancement of collateral blood flow to ischemic myocardium by vascular endothelial growth factor in dogs," *Circulation* 89(5): 2183-2189 (1994).
Banks, et al., "Release of the angiogenic cytokine vascular endothelial growth factor (VEGF) from platelets: significance for VEGF measurements and cancer biology," *Br. J. Cancer* 77(6): 956-964 (1998).
Baumgartner, et al., "Constitutive expression of phVEGF165 after intramuscular gene transfer promotes collateral vessel development in patients with critical limb ischemia," *Circulation* 97(12): 1114-1123 (1998).
Baumgartner, et al., "Somatic gene therapy in the cardiovascular system," *Annu. Rev. Physiol.* 63: 427-450 (2001).
Bauters, et al., "Recovery of disturbed endothelium-dependent flow in the collateral-perfused rabbit ischemic hindlimb after administration of vascular endothelial growth factor," *Circulation* 91(11): 2802-2809 (1995).
Bauters, et al., "Site-specific therapeutic angiogenesis after systemic administration of vascular endothelial growth factor," *J. Vasc. Surg.* 21(2): 314-325 (1995).
Beer, et al., "Reduced expression of PDGF and PDGF receptors during impaired wound healing," *J. Invest. Dermatol.* 109(2): 132-138 (1997).
Bennett, "Growth factors in the treatment of diabetic foot ulcers." *British Journal of Surgery* 90:133-46 (2003).
Berse, et al., "Vascular permeability factor (vascular endothelial growth factor) gene is expressed differentially in normal tissues, macrophages, and tumors," *Mol. Biol. Cell* 3(2): 211-220 (1992).
Bessman & Sapico, "Infections in the diabetic patient: the role of immune dysfunction and pathogen virulence factors," *J. Diabetes Complications* 6(4): 258-262 (1992).
Bett, et al., "Packaging capacity and stability of human adenovirus type 5 vectors," *J. Virol.* 67(10): 5911-5921 (1993).

(Continued)

*Primary Examiner* — Robert M Kelly
(74) *Attorney, Agent, or Firm* — Pabst Patent Group LLP

(57) ABSTRACT

A method and means have been developed to deliver a therapeutic dose or dosages of the angiogenic molecule, Vascular Endothelial Growth Factor (VEGF) that results in a statically significant decrease in the time to achieve 100% wound closure and accelerates the rate of healing in experimental diabetic ulcers. Toxicity is evaluated by measuring any local inflammatory response at the wound site, the systemic absorption of VEGF, and the effect on distant organs that may be particularly susceptible to VEGF therapy (e.g., retinopathy and hepatitis) The angiogenic response is quantified by measuring the change in collagen deposition, epithelialization, and the closure rates of diabetic ulcers after therapeutic dosing with ADV-VEGF. Sustained administration of VEGF, stimulates and accelerates the healing process as evidenced by a reduced time to complete healing (defined by 100% epithelialization and no drainage) in experimental diabetic ulcers, with minimal to no toxicity. Important features of the method and reagents for use therein are that the VEGF is released into the ulcer in a sufficient quantity over a period of time for at least two to six weeks, or to closure of the wound.

8 Claims, 1 Drawing Sheet

OTHER PUBLICATIONS

Bramson, et al., "Pre-existing immunity to adenovirus does not prevent tumor regression following intratumoral administration of a vector expressing IL-12 but inhibits virus dissemination," *Gene Ther.* 4(10): 1069-1076 (1997).

Brem & Folkman, "Angiogenesis and basic firbroblast growth factor during wound healing," in *Bone Formation and Repair* (Brighton, et al., eds.) American Academy of Orthopaedic Surgeons: Rosemont, Illinois, pp. 213-222 (1994).

Brem, et al., "Healing of diabetic foot ulcers and pressure ulcers with human skin equivalent," *Arch. Surg.* 135: 627-634 (2000).

Brogi, et al., "Indirect angiogenic cytokines upregulate VEGF and bFGF gene expression in vascular smooth muscle cells, whereas hypoxia upregulates VEGF expression only," *Circulation* 90(2): 649-652 (1994).

Brown, et al., "Differential expression and localization of insulin-like growth factors I and II in cutaneous wounds of diabetic and nondiabetic mice," *Am. J. Pathol.* 151(3): 715-724 (1997).

Brown, et al., "PDGF and TGF-alpha act synergistically to improve wound healing in the genetically diabetic mouse," *J. Surg. Res.* 56(6): 562-570 (1994).

Coleman, "Diabetes-obesity syndromes in mice," *Diabetes* 31(Suppl 1; Pt 2): 1-6 (1982).

Connolly, et al., "Tumor vascular permeability factor stimulates endothelial cell growth and angiogenesis," *J. Clin. Invest.* 84(5): 1470-1478 (1989).

Corral, et al., "Vascular endothelial growth factor is more important than basic fibroblastic growth factor during ischemic wound healing," *Arch. Surg.* 134(2): 200-205 (1999).

Darby, et al., "Apoptosis is increased in a model of diabetes-impaired wound healing in genetically diabetic mice," *Int. J. Biochem. Cell Biol.* 29: 191-200 (1997).

Esakof, et al., "Intraoperative multiplane transesophageal echocardiography for guiding direct myocardial gene transfer of vascular endothelial growth factor in patients with refractory angina pectoris," *Hum. Gene Ther.* 10(14): 2307-2314 (1999).

Feige & Van Eden, "Infection, autoimmunity and autoimmune disease," *EXS* 77: 359-373 (1996).

Feng, et al., "Neoplastic reversion accomplished by high efficiency adenoviral-mediated delivery of an anti-ras ribozyme," *Cancer Res.* 55(10): 2024-2028 (1995).

Ferrara & Henzel, "Pituitary follicular cells secrete a novel heparin-binding growth factor specific for vascular endothelial cells," *Biochem. Biophys. Res. Comm.* 161(2): 851-858 (1989).

Ferrara, "Molecular and biological properties of vascular endothelial growth factor," *J. Mol. Med.* 77(7): 527-543 (1999).

Folkman & Brem, "Angiogenesis and inflammation," in *Inflammation: Basic Principles and Clinical Correlates*, 2$^{nd}$ ed., (Gallin, et al., eds.) Raven Press: New York, pp. 821-839 (1992).

Folkman, "The angiogenic activity of FGF and its possible clinical applications," in *Growth Factors: From Genes to Clinical Application* (Sara, et al., eds.) Raven Press: New York, NY, pp. 201-216 (1990).

Frank, et al., "Regulation of vascular endothelial growth factor expression in cultured keratinocytes. Implications for normal and impaired wound healing," *J. Biol. Chem.* 270(21): 12607-12613 (1995).

Geerlings, et al., "Immune dysfunction in patients with diabetes mellitus (DM)," *FEMS Immunol. Med. Microbiol.* 26(3-4): 259-265 (1999).

Gennaro, et al., "Age-dependent impairment of reendothelialization after arterial injury: role of vascular endothelial growth factor," *Circulation* 107(2): 230-233 (2003).

Gospodarowicz & Schilling, et al., "Isolation and characterization of a vascular endothelial cell mitogen produced by pituitary-derived folliculo stellate cells," *Proc. Natl. Acad. Sci. USA* 86(19): 7311-7315 (1989).

Greenhalgh, et al., "PDGF and FGF stimulate wound healing in the genetically diabetic mouse," *Am. J. Pathol.* 36(6): 1235-1246 (1990).

Hammond & McKirnan, et al., "Angiogenic gene therapy for heart disease: a review of animal studies and clinical trials," *Cardiovasc. Res.* 49(3): 561-567 (2001).

Hariawala, et al., "VEGF improves myocardial blood flow but produces EDRF-mediated hypotension in porcine hearts," *J. Surg. Res.* 63: 77-82 (1996).

Hebda, et al., "Basic fibroblast growth factor stimulation of epidermal wound healing in pigs," *J. Invest. Dermatol.* 95(6): 626-631 (1990).

Hendel, et al., "Effect of intracoronary recombinant human vascular endothelial growth factor on myocardial perfusion: evidence for a dose-dependent effect," *Circulation* 101(2); 118-121 (2000).

Hunt, et al., "Studies on inflammation and wound healing: angiogenesis and collagen synthesis stimulated in vivo by resident and activated wound macrophages," *Surgery* 96: 48-54 (1984).

Isner, et al., "Arterial gene transfer for therapeutic angiogenesis in patients with peripheral artery disease," *Hum. Gene Ther.* 7(8): 959-988 (1996).

Isner, et al., "Clinical evidence of angiogenesis after arterial gene transfer of phVEGF16 in patient with ischaemic limb," *Lancet* 348(9024): 370-374 (1996).

Isner, et al., "Treatment of thromboangitis obliterans (Buerger's disease) by intramuscular gene transfer of vascular endothelial growth factor: preliminary clinical results," *J. Vasc. Surg.* 28(6): 964-75 (1998).

Jiao, et al., "Persistence of plasmid DNA and expression in rat brain cells in vivo," *Exp. Neurol.* 115: 400-413 (1992).

Kaner, et al., "Lung overexpression of the vascular endothelial growth factor gene induces pulmonary edema," *Am. J. Respir. Cell Mol. Biol.* 22(6): 657-664 (2000).

Keck, et al., "Vascular permeability factor, an endothelial cell mitogen related to PDGF," *Science* 246(4935): 1309-1312 (1989).

Koch, at al., "Interleukin-8 as a macrophage-derived mediator of angiogenesis," *Science* 258(5089): 1798-1801 (1992).

Kozarsky & Wilson, "Gene therapy: adenovirus vectors," *Curr. Opin. Genet. Dev.* 3(3): 499-603 (1993).

Kremer & Perricaudet, "Adenovirus-mediated gene transfer," *Gene Ther.* 2: 564-565 (1995).

Laitinen, et al "Catheter-mediated vascular endothelial growth factor gene transfer to human coronary arteries after angioplasty," *Hum. Gene Ther.* 11(2): 263-270 (2000).

Lauer, et al., "Expression and proteolysis of vascular endothelial growth factor is increased in chronic wounds," *J. Invest. Derm.* 115: 12-18 (2000).

Lazarous, et al., "Adenoviral-mediated gene transfer induces sustained pericardial VEGF expression in dogs: effect on myocardial angiogenesis," *Cardiovasc. Res.* 44(2): 294-302 (1999).

Leibovich & Ross, "The role of the macrophage in wound repair. A study with hydrocortisone and antimacrophage serum," *Am. J. Pathol.* 78: 71-100 (1975).

Lerman, et al., "Cellular dysfunction in the diabetic fibroblast: impairment in migration, vascular endothelial growth factor production, and response to hypoxia," *Am. J. Pathol.* 162: 303-312 (2003).

Leung, et al., "Vascular endothelial growth factor is a secreted angiogenic mitogen," *Science* 246(4935): 1306-1309 (1989).

Li, et al., "Human recombinant vascular endothelial growth factor accelerates maturation of rat tail artery prefabricated flap," *Surg Forum.* 50: 586-587 (1999).

Liao, et al., "Oxidized low-density lipoprotein decreases the expression of endothelial nitric oxide synthase," *J. Biol. Chem.* 270: 319-324 (1995).

Liechty, et al., "Adenoviral-mediated overexpression of platelet-derived growth factor-B corrects ischemic impaired wound healing," *J. Invest. Dermatol.* 113(3): 375-383 (1999).

Liechty, et al., "Recombinant adenoviral mediated gene transfer in ischemic impaired wound healing," *Wound Repair Regen.* 7(3): 148-153 (1999).

Livant, et al., "The PHSRN sequence induces extracellular matrix invasion and accelerates wound healing in obese diabetic mice," *J. Clin. Invest.* 105(11): 1537-1545 (2000).

Loots, et al., "Differences in cellular infiltrate and extracellular matrix of chronic diabetic and venous ulcers versus acute wounds," *J. Invest. Dermatol.* 111(5): 850-857 (1998).

Lopez, et al., "VEGF administration in chronic myocardial ischemia in pigs," *Cardiovasc. Res.* 40(2): 272-281 (1998).

Losordo, et al., "Gene therapy for myocardial angiogenesis," *Am. Heart J.* 138: S132-S141 (1999).

Losordo, et al., "Gene therapy for myocardial angiogenesis: initial clinical results with direct myocardial injection of phVEGF165 as sole therapy for myocardial ischemia," *Circulation* 98(25): 2800-2804 (1998).

Maragoudakis, "Angiogenesis in health and disease," *Gen. Pharmacol.* 35: 225-226 (2002).

Margolis, "Healing diabetic neuropathic foot ulcers: are we getting better?" *Diabetic Medicine*, 22(2):172-176(2005).

Matsuda, et al., "Role of nerve growth factor in cutaneous wound healing: accelerating effects in normal and healing-impaired diabetic mice," *J. Exp. Med.* 187(3): 297-306 (1998).

Matuszewska, et al., "Acidic fibroblast growth factor: evaluation of topical formulations in a diabetic mouse wound healing model," *Pharm. Res.* 11: 65-71 (1994).

Mitani, et al., "Rescue, propagation, and partial purification of a helper virus-dependent adenovirus vector," *Proc. Natl. Acad. Sci. USA* 92(9): 3854-3858 (1995).

Molnar-Kimber, et al., "Impact of preexisting and induced humoral and cellular immune responses in an adenovirus-based gene therapy phase I clinical trial for localized mesothelioma," *Hum. Gene Ther.* 9(14): 2121-2133 (1998).

Mühlhauser, et al., "VEGF165 expressed by a replication-deficient recombinant adenovirus vector induces angiogenesis in vivo," *Circ. Res.* 77(6): 1077-1086 (1995).

Mulligan, "The basic science of gene therapy," *Science* 260(5110): 926-32 (1993).

Nabel, et al., "Direct gene transfer with DNA-liposome complexes in melanoma: expression, biologic activity, and lack of toxicity in humans," *Proc. Natl. Acad. Sci. USA* 90(23): 11307-11311 (1993).

Nabel, et al., "Site-specific gene expression in vivo by direct gene transfer into the arterial wall," *Science* 249(4974): 1285-1288 (1990).

Nakanashi, et al., "Improved airway healing using basic fibroblast growth factor in a canine tracheal autotransplantation," *Ann. Surg.* 227(3): 446-454 (1998).

Namiki, et al., "Hypoxia induces vascular endothelial growth factor in cultured human endothelial cells," *J. Biol. Chem.* 270(52): 31189-31195 (1995).

Nathan, "Secretory products of macrophages," *J. Clin. Invest.* 79(2): 319-326 (1987).

Nissen, et al., "Vascular endothelial growth factor mediates angiogenic activity during the proliferative phase of wound healing," *Am. J. Pathol.* 152(6): 1445-1452 (1998).

Padubidri & Browne Jr., "Effect of vascular endothelial growth factor (VEGF) on survival of random extension of axial pattern skin flaps in the rat," *Ann. Plast. Surg.* 37(6): 604-611 (1996).

Pasini, et al., "Peripheral neuropathy associated with ischemic vascular disease of the lower limbs," *Angiology* 47(6): 569-577 (1996).

Pearlman, et al., "Magnetic resonance mapping demonstrates benefits of VEGF-induced myocardial angiogenesis," *Nat. Med.* 1(10): 1085-1089 (1995).

Pecoraro, et al., "Pathways to diabetic limb amputation. Basis for prevention," *Diabetes Care* 13(5): 513-521(1990).

Pettet, et al., "On the role of angiogenesis in wound healing," *Proc R. Soc. Lond. B Biol. Sci.* 263(1376): 1487-1493 (1996).

Reiber, et al., eds., *Diabetes in America* U.S. Government Printing Office: Washington, DC, pp. 409-428 (1995).

Richard, et al., "Effect of topical basic fibroblast growth factor on the healing of chronic diabetic neuropathic ulcer of the foot. A pilot, randomized, double-blind, placebo-controlled study," *Diabetes Care* 18(1): 64-69 (1995).

Rivard, et al., "Rescue of diabetes-related impairment of angiogenesis by intramuscular gene therapy with adeno-VEGF," *Am. J. Pathol.* 154(2): 355-363 (1999).

Romando Di Peppe, et al., "Adenovirus-mediated VEGF(165) gene transfer enhances wound healing by promoting angiogenesis in CD1 diabetic mice," *Gene Therapy* 9(19): 1271-1277 (2002).

Samii, et al., "Vascular endothelial growth factor expression in peripheral nerves and dorsal root ganglia in diabetic neuropathy in rats," *Neurosci. Lett.* 262(3): 159-162 (1999).

Sauter, et al., "Adenovirus-mediated gene transfer of endostatin in vivo results in high level of transgene expression and inhibition of tumor growth and metastases," *Proc. Natl. Acad. Sci. USA* 9(9): 4802-4807 (2000).

Schratzberger, et al., "Favorable effect of VEGF gene transfer on ischemic peripheral neuropathy," *Nat. Med.* 6(4): 405-413 (2000).

Schratzberger, et al., "Reversal of experimental diabetic neuropathy by VEGF gene transfer," *J. Clin. Invest.* 107(9): 1083-1092 (2001).

Seifert, et al., "Quantitation of angiogenesis in healing anastomoses of the rat colon," *Exp. Mol. Pathol.* 64(1): 31-40 (1997).

Senger, et al., "Purification and NH2-terminal amino acid sequence of guinea pig tumor-secreted vascular permeability factor," *Cancer Res.* 50(6): 1774-1778 (1990).

Simovic, et al., "Improvement in chronic ischemic neuropathy after intramuscular phVEGF165 gene transfer in patients with critical limb ischemia," *Arch. Neurol.* 58(5): 761-768 (2001).

Stavri, et al., "Basic fibroblast growth factor upregulates the expression of vascular endothelial growth factor in vascular smooth muscle cells. Synergistic interaction with hypoxia," *Circulation* 92(1): 11-14 (1995).

Stehouwer, et al., "Endothelial dysfunction and pathogenesis of diabetic angiopathy," *Cardiovasc. Res.* 34(1): 55-68 (1997).

Sun, et al., "Transfection with aFGF cDNA improves wound healing," *J. Invest. Dermatol.* 108(3): 313-318 (1997).

Sylvén, et al., "Myocardial Doppler tissue velocity improves following myocardial gene therapy with VEGF-A165 plasmid in patients with inoperable angina pectoris," *Coron. Artery Dis.* 12(3): 239-243 (2001).

Symes, et al., "Gene therapy with vascular endothelial growth factor for inoperable coronary artery disease," *Ann. Thorac. Surg.* 68(3): 830-837 (1999).

Takeshita, et al., "Intramuscular administration of vascular endothelial growth factor induces dose-dependent collateral artery augmentation in a rabbit model of chronic limb ischemia," *Circulation* 90(5.2): II228-234 (1994).

Takeshita, et al., "Therapeutic angiogenesis following arterial gene transfer of vascular endothelial growth factor in a rabbit model of hindlimb ischemia," *Biochem Biophys Res Commun.* 227(2): 628-635 (1996).

Takeshita, et al., "Therapeutic angiogenesis. A single intraarterial bolus of vascular endothelial growth factor augments revascularization in a rabbit ischemic hind limb model," *J. Clin. Invest.* 93(2): 662-670 (1994).

Thornton, et al., "Transfection of the inducible nitric oxide synthase gene increases reparative wound collagen accumulation," *Surg. Forum* 667-669 (1997).

Tio, et al., "Intramyocardial gene therapy with naked DNA encoding vascular endothelial growth factor improves collateral flow to ischemic myocardium," *Hum. Gene Ther.* 10(18): 2953-2960 (1999).

Tsuboi & Rifkin, "Recombinant basic fibroblast growth factor stimulates wound healing in healing-impaired db/db mice," *J. Exp. Med.* 172: 245-251 (1990).

Tsurumi, et al., "Direct intramuscular gene transfer of naked DNA encoding vascular endothelial growth factor augments collateral development and tissue perfusion," *Circulation* 94(12): 3281-3290 (1996).

Uchida, et al., "Glomerular endothelial cells in culture express and secrete vascular endothelial growth factor," *Am. J. Physiol.* 266(1.2): F81-F88 (1994).

Vale, et al., "Left ventricular electromechanical mapping to assess efficacy of phVEGF(165) gene transfer for therapeutic angiogenesis in chronic myocardial ischemia," *Circulation* 102(9): 965-974 (2000).

Veves, et al., "Endothelial dysfunction and the expression of endothelial nitric oxide synthetase in diabetic neuropathy, vascular disease, and foot ulceration," *Diabetes* 47(3): 457-463 (1998).

Vincent, et al., "Angiogenesis is induced in a rabbit model of hindlimb ischemia by naked DNA encoding an HIF'1alpha/VP16 hybrid transcription factor," *Circulation* 102(18): 2255-2261 (2000).

Werner, et al., "Induction of keratinocyte growth factor expression is reduced and delayed during wound healing in the genetically diabetic mouse," *J. Invest. Dermatol.* 103(4): 469-473 (1994).

Wetzler, et al., "Large and sustained induction of chemokines during impaired wound healing in the genetically diabetic mouse: prolonged persistence of neutrophils and macrophages during the late phase of repair," *J. Invest. Dermatol.* 115(2): 245-253 (2000).

Witte, et al., "Nitric oxide enhances wound collagen depositions in diabetic rats," *Surg. Forum* 48: 665-666 (1997).

Wolff, et al., "Direct gene transfer into mouse muscle in vivo," *Science* 247(4949.1): 1465-1468 (1990).

Wong, et al., "Fibrin-based biomaterials to deliver human growth factors," *Thromb. Haemost.* 89(3): 573-582 (2003).

Yamamoto, et al., "Effect of topical application of a stable prostacyclin analogue, SM-10902 on wound healing in diabetic mice," *Eur. J. Pharmacol.* 302(1-3): 53-60 (1996).

Yang, et al., "MHC class I-restricted cytotoxic T lymphocytes to viral antigens destroy hepatocytes in mice infected with E1-deleted recombinant adenoviruses," *Immunity* 1(5): 433-442 (1994).

Yoshida, et al., "Differential endothelial migration and proliferation to basic fibroblast growth factor and vascular endothelial growth factor," *Growth Factors* 13(1-2): 57-64 (1996).

Zykova, et al., "Altered cytokine and nitric oxide secretion in vitro by macrophages from diabetic type II-like db/db mice," *Diabetes* 49(9): 1451-1458 (2000).

* cited by examiner

METHOD FOR TREATING DIABETIC ULCERS WITH VECTORS ENCODING VEGF

CROSS REFERENCE TO RELATED APPLICATIONS

This application is a continuation of U.S. Ser. No. 10/388,825 filed Mar. 12, 2003, by Harold Brem, which claims priority to U.S. Ser. No. 60/363,584 filed Mar. 12, 2002, both of which are incorporated by reference in their entirety.

The United States government has certain rights in this invention by virtue of a NIH, National Institute of Diabetes and Digestive and Kidney Diseases (NIDDK) grant R21DK060214-01 and NIH, National Institute of Diabetes and Digestive and Kidney Diseases (NIDDK) grant K08DK059424-01 to Dr. Harold Brem.

BACKGROUND OF THE INVENTION

The present invention is a method of tissue engineering, and specifically relates to administration of angiogenic factors directly to diabetic wound ulcers, in an effective amount for a sustained period of time effective to promote closure.

Among the 16 million diabetic patients (diagnosed and undiagnosed) in the United States, an estimated 1200 amputations are performed each week (Pecoraro, et al., *Diabetes Care*. 1990; 13:213-521); 84% of which are preceded by a foot ulcer. Limb amputation in diabetics is associated with an increased risk for further amputation, with a five-year mortality rate of 39 to 68% (Reiber et al. *Diabetes in America*. Washington, D.C.; U.S. Government Printing Office, 1995: 409-428). The direct costs of a lower extremity amputation range from $20,000 to $60,000. When failed vascular reconstruction, rehabilitation, and lost productivity within society are considered, these costs greatly exceed financial analysis. The grave consequences, pain, and suffering endured by patients with diabetic foot ulcers mandate determination of the best combination of therapies to prevent progression and, consequent occurrence of these complications.

In addition to amputation, the need to have accelerated healing in diabetic patients with foot ulcers is accentuated because these patients have impaired immunity (Geerlings et al. *FEMS Immunol Med Microbiol*. 1999; 3-4:259-265; Feige et al., *EXS*. 1996; 77:359-373; Bessman et al., *J Diabetes Complications*. 1992; 4:258-262; Abraham, et al., *J Dermatol*. 1990; 7440-447; Loots et al., *J Invest Dermatol*. 1998; 5:850-857; Brown et al., *J Surg Research* 1994; 56:562-570; Greenhalgh et al., *Am J Pathol* 1990; 1361235-1246). Since unhealed open wounds are portals for systemic infection, they can have particularly devastating effects for the diabetic patient.

It is well known that diabetic patients are predisposed to ulceration. This predisposition has multiple etiologies, including endothelial cell dysfunction, accelerated atherosclerosis, and peripheral neuropathy, which relate to the endothelium and contribute to deficits in healing. One of the most central etiologies for this predisposition is the reduced angiogenic response in the diabetic patient.

Recently, local use of growth factors has been shown to be promising for the treatment of diabetic ulcers. Two new agents have been FDA approved for the treatment of diabetic foot ulcers. The first, platelet derived growth factor (PDGF-BB), has shown efficacy. The second, human skin equivalent, has also shown efficacy in the treatment of diabetic foot ulcers. However, despite their successes, there remain several significant problems with these therapies: neither has demonstrated efficacy in ischemic diabetic foot ulcers, and both have a minimum failure rate of 45% in well vascularized limbs. Although this is better than the failure rate of standard therapies (i.e., off-loading and saline dressing), the number of amputations and non-healed diabetic foot ulcers remains excessive. Although both of these therapies have also demonstrated that local therapy is clinically effective in the treatment of diabetic foot ulcers, more therapies are clearly needed.

Therefore, it is an object of the present invention to provide a method and means to provide increased blood flow to diabetic ulcers, and thereby promote wound closure.

SUMMARY OF THE INVENTION

A method and means have been developed to deliver a therapeutic dose or dosages of the angiogenic molecule, Vascular Endothelial Growth Factor (VEGF) that results in a statistically significant decrease in the time to achieve substantially 100% wound closure and accelerates the rate of healing in experimental diabetic ulcers. Toxicity is evaluated by measuring any local inflammatory response at the wound site, the systemic absorption of VEGF, and the effect on distant organs that may be particularly susceptible to VEGF therapy (e.g., retinopathy and hepatitis) The angiogenic response is quantified by measuring the change in collagen deposition, epithelialization, and the closure rates of diabetic ulcers after therapeutic dosing with adenoviral vector (ADV)-VEGF or VEGF. Sustained administration of VEGF stimulates and accelerates the healing process as evidenced by a reduced time to complete healing (defined by 100% epithelialization and no drainage) in experimental diabetic ulcers, with minimal to no toxicity. Important features of the method and reagents for use therein are that the VEGF is released into the ulcer in a sufficient quantity over a period of time for at least two to six weeks, or to closure of the wound. The VEGF can be administered directly or as the gene which is expressed at the site in need of treatment.

DETAILED DESCRIPTION OF THE INVENTION

VEGF and Angiogenesis

Figure 1:
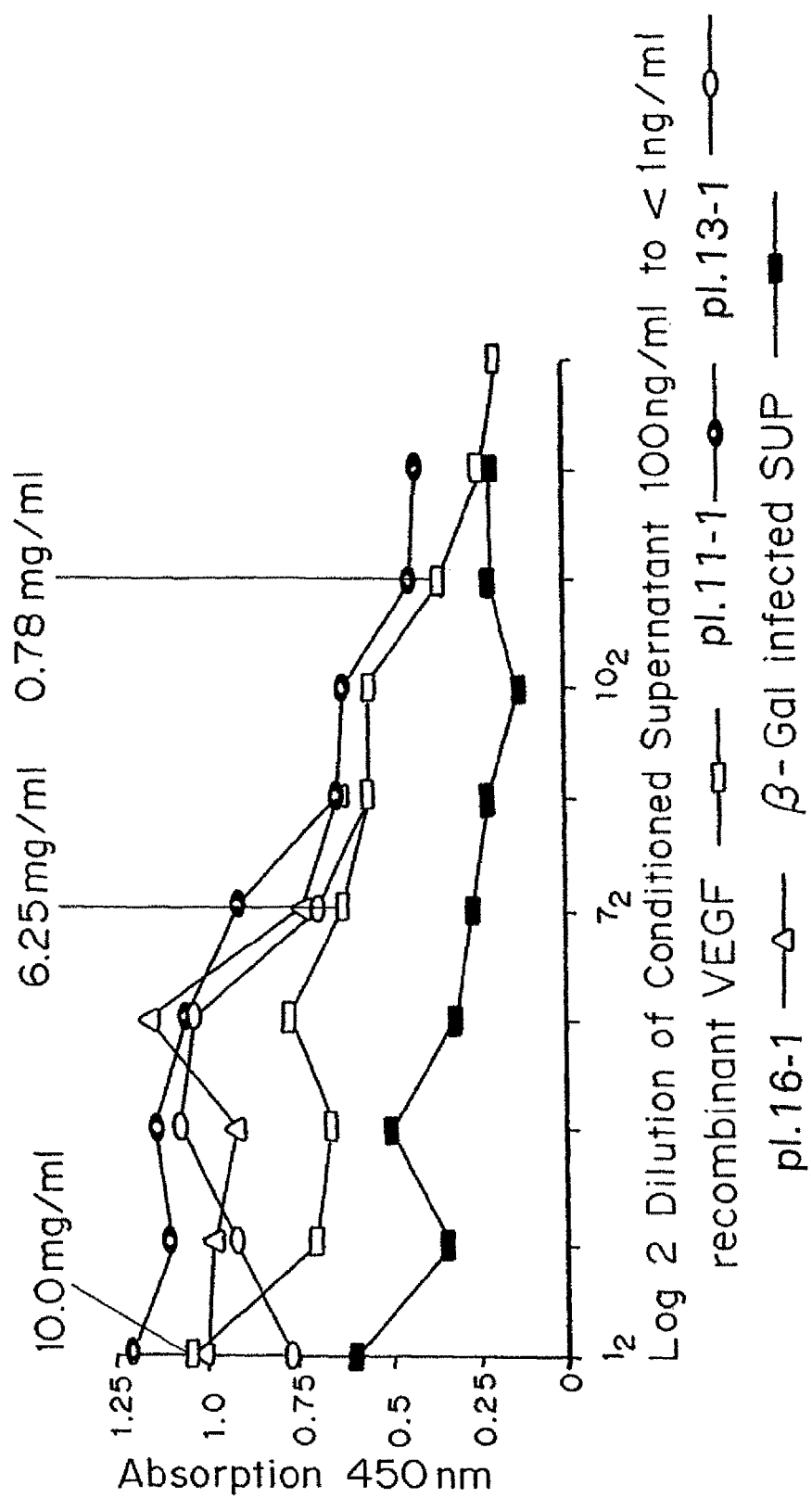
FIG. 1 is a graph of the proliferation of human vascular endothelial cells (HUVECs) stimulated with the supernatant of JC cells infected with adenoviral vectors expressing VEGF, as a function of number of cells (absorption) versus dilution of conditioned supernatant, compared to control (beta-galactosidase).

Local angiogenic therapy is used to treat one of the primary etiologies of complications in patients with diabetic foot ulcers, decreased angiogenesis in the wound. It has been well established that distal bypass alone is not enough to sufficiently accelerate the healing of most diabetic foot ulcers.

There are multiple physiological processes that result in decreased angiogenesis in a diabetic ulcer; including:

1. Decreased VEGF expression in experimental diabetic wounds. VEGF normally stimulates endothelial cell proliferation and experimental diabetic wounds show a marked decrease in angiogenesis (Frank et al., *J Biol Chem* 1995; 270:12607-12613; Tsuboi, et al., *J Explorer Med* 1990; 172:245-251).
2. Endothelial dysfunction results in several metabolic anomalies in diabetes, including oxidative stress, hyperglycemic pseudohypoxia, nonenzymatic glycosylation, and activation of the coagulation cascade (Stehouwer et al., *Cardiovasc Res* 1997; 34:55-68)

3. Accelerated atherosclerosis may impair function by damaging the transduction cascades that synthesize nitrous oxide or by decreasing expression of nitrous oxide synthase, consistent with the finding of decreased nitrous oxide synthase expression in skin endothelium from diabetic patients (Liao, et al., *J Biol Chem* 1995; 270:319-324; Veves et al., *Diabetes* 1998; 47:457-463).

4. Neuropathy is associated with endothelium dependent and independent dysfunction in diabetic patients, predisposing them to foot ulceration (Pasini et al., *Angiology* 1996; 47:569-577).

5. Arterial occlusive disease is associated with peripheral neuropathy, manifested as slower conduction velocity of motor and sensory nerves and depression of automatic responses.

Other factors are thought to be significant variables in the treatment of diabetic wound ulcers, especially the high pressure within the wound, which contributes to the ischemia and neuropathy, although it has not been apparent what single factor, if any, could be effective in promoting wound closure.

VEGF has been shown to be efficacious in the treatment of cardiac ischemia and leg ischemia, and it has demonstrated effectiveness in the treatment of diabetic limbs. However, it has not previously been tested in diabetic ulcers. VEGF possesses certain key advantages for use in diabetic foot ulcers over other angiogenic agents, for example, basic fibroblast growth factor (bFGF). Although bFGF has been one of the most widely studied angiogenic growth factors for the treatment of experimental diabetic ulcers (Albertson et al. *Surgery* 1993; 114:368-373), other chronic wounds (Quirinia, et al., *Ann Surg* 1998; 227:446-454), and accelerating acute wound healing (Hebda et al., *J Invest Dermatol* 1990; 95:626-631), it has not been shown to be effective in treating human diabetic ulcers (Richard, et al., *Diabetes Care* 1995; 18:64-69). Unlike VEGF, bFGF is not acid stable, which is critical in the low pH environment of a diabetic wound (Ferrara, et al., *Biochem Biophys Res Comm* 1989; 161:851-858). The impaired wound healing in diabetics may be due to fibroblast dysfunction (Lerman et al. Am. J. Pathol. 2003; 162:303-312). Fibroblasts from diabetic db/db mice maintain selective impairments in multiple cellular processes which are accentuated by hypoxic environments such as those in a healing wound. These impairments include a severe reduction in VEGF expression, and release in response to injury. These changes were only observed after the development of the diabetic phenotype in these animals. Additionally, VEGF has been shown to be a more potent angiogenic molecule than bFGF in experimental diabetic wound (Corral, et al., *Arch Surg.* 199; 134:200-5). Also, VEGF levels are apparently decreased by endogenous proteases (Lauer, et al., *J Invest Derm* 2000; 115:12-18) in chronic wounds. This provides a basis from which to develop gene therapy with VEGF for use in diabetic wounds. The intense and sustained local synthesis of VEGF by local angiogenic therapy should obviate the proteolytic degradation of endogenous VEGF in the diabetic wound.

The role of VEGF in angiogenesis reflects its function as an endothelial cell mitogen, (Ferrara N., *J Mol Med* 1999; 77:524-543; Gospodarowicz D, et al., *Proc Natl Acad Sci* 1989; 86:7311-7315) chemotactic agent, (Leung D W, et al., *Science* 1989; 246:1306-1309; Keck P J, et al., *Science* 1989; 246:1309-1312) and inducer of vascular permeability (Connolly D T, et al., *J Clin Invest* 1989; 84:1470-1478; Yoshida A, et al, *Growth Factors* 1996; 13:57-64; Senger D R, et al., *Cancer Res* 1990; 50:1774-1778). It exists in many isoforms with a common amino terminus that contains a signal sequence that allows the protein to be secreted. $VEGF_{165}$ is the most common isoform and is preferred, although it is understood that other equivalent forms of VEGF are known and could be used alone or in combination with each other as described herein.

Many of the cells (Banks, et al., *Br J Cancer* 1998; 77:956-964, Nathan, *J Clin Invest* 1987; 79:319-326; Berse, et al., *Mol Biol Cell* 1992; 3:211-220; Leibovich, et al., *Am J Pathol* 1975; 78:71-100; Koch, et al., *Science* 1993; 258:1798-1801; Uchida, et al., *Am J Physol* 1994; 266:F81-F88; Namiki, et al., *J Biol Chem* 1995; 270:31189-31195; Nissen, et al., *Am J Path* 1998; 152:1445-1452; Brogi, et al., *Circulation* 1994; 90:649-652; Stavri, et al. *Circulation* 1995; 92:11-14) recruited into a wound synthesize VEGF. VEGF serves distinct paracrine and autocrine roles upon endothelial cells. By stimulating the endothelial cells, multiple phases of the angiogenic cascade are enhanced by VEGF. VEGF has been shown in experimental studies to enhance vascularization of both autologous bone grafts and skin flaps in rats (Padubidri, et al., *Ann Plast Surg* 1996; 37:604-611; Li, et al. *Surg Forum.* 1999; 50:586-587). One of the mediators of VEGF activity, nitric oxide, enhances collagen deposition in diabetic wounds, (Witte, et al., *Surg Forum* 1997:48:665-667) and may restore endothelial function to improve both nerve conduction and tissue oxygenation. This supports the concept that VEGF enhances wound healing primarily by stimulating angiogenesis and possible secondary stimulation of collagen production.

Local Sustained Release of VEGF in a Diabetic Wound

In the twelve years that VEGF has been available, local therapy with recombinant forms has not yet been shown to be effective for wound closure. One limitation to this technique is that it fails to sustain sufficient levels of VEGF in the wound for a significant period of time. Gene therapy is an effective means for delivering VEGF in a sustained release fashion in vivo. ADV-VEGF has already been tested in patients with cardiac ischemia and leg ischemia to stimulate angiogenesis. Additionally, it has also been tested for diabetic ischemia and neuropathy. Other means of obtaining sustained release of an effective amount of compound include providing sustained release formulations such as polymeric delivery systems, mini-pumps, and hydrogels. These can be loaded with VEGF, injected or implanted into the ulcers, where the VEGF is released over a therapeutically effective time period.

The principle of gene therapy is that a therapeutic gene must first be efficiently delivered to the specific target cell Nabel, et al., *Science.* 1990; 249:1285-1288). Second, it must be expressed and sustained at a certain level to achieve its therapeutic purpose (Sauter, et al., *Proc Natl Acad Sci USA.* 2000; 9:4802-4807).

The principle components of gene therapy are a vector or other means of delivering a nucleic acid of interest, and the nucleic acid. Many appropriate viral vectors are known, most of which are adenoviral vectors, adeno-associated viral vectors or retroviral vectors. Other means of delivery include liposomes, direct delivery of naked DNA, and hydrogels. The vectors will typically include a promoter that can contain enhancers, inverted terminal repeats (ITRs), inducible promoters, and polyA sequences, followed by a termination sequence. All of these are known to those skilled in the art, and commercially available or described in the literature.

The discovery that naked DNA is taken up by muscle cells and transiently expressed in vivo, was reported twelve years ago, by Wolff, al, et, *Science,* 1990; 247, 1465-1468; and Wolff, *Nature,* 1991; 352, 815-818.

Plasmid DNA, which can function episomally, has been used with liposome encapsulation, $CaPO_4$ precipitation, and electroporation as an alternative to viral transfections. Clinical trials with liposome encapsulated DNA in treating melanoma illustrates this approach to gene therapy, as reported by Nabel, et al., *Proc. Nat. Acad. Sci. U.S.A.,* 1993; 90, 11307-11311 and Wolff, *Experimental Neurology,* 1992; 115, 400-413, also reported expression of plasmid DNA, There have been many confirmatory reports since the initial studies.

Viral vectors are preferred for gene therapy. Human adenoviruses have a 36-kilobase double-stranded DNA genome that undergoes a highly regulated program of gene expression during the normal life cycle of the virus. The advantages of adenoviruses over other chemical, physical, or biological gene transfer techniques include several unique features of this system (Molnar-Kimber et al., *Hum Gene Ther* Sep. 20, 1998; 9(14):2121-33). First, adenoviruses infect human skin cells at more than 95% efficiency and do not require that cells are dividing, making a lengthy selection process unnecessary (Kozarsky, et al., *Curr Opin Genet Dev* June 1993; 3(3):499-503; Mulligan, *Science* May 14, 1993; 260(5110):926-32; Kremer, *Gene Ther* 1995; 2:564-5; Yang, et al., *Immunity* August 1994; 1(5):433-42; Mitani, et al., *Proc Natl Acad Sci USA* Apr. 25, 1995; 92(9):3854-8). Second, adenoviruses remain episomal and thus do not normally integrate into the human genome (Bett, et al., *J Virol* October 1993; 67(10): 5911-21; Losordo, et al., *Am Heart J.* 1999; 138:132-141) Third, adenovirus-mediated gene expression in keratinocytes, melanocytes, and fibroblasts remains stable in vitro for at least 2-6 weeks, depending on the proliferation rate of cells (Feng, et al., *Cancer Res May* 15, 1995; 55(10):2024-8). Adenoviral vectors are commonly constructed by deletion of the essential ELAM-1 gene to prevent viral replication.

For the purpose of wound healing, ADV-VEGF gene therapy may offer substantial advantages, one of which is its ability to transduce both resting and dividing cells at very high efficiency without integration into the host cell's genome. The inflammatory response that is often associated with adenoviral mediated gene transfer for the induction of endogenous growth factor overexpression may actually enhance wound healing, since wound healing is itself fundamentally an inflammatory response. Furthermore, the limited duration of high level transgene expression of a growth factor known to have significant vulnerary effects (like VEGF) may be all that is necessary to affect wound healing. Recombinant ADV can be generated in high titers, is known to infect both resting and dividing cells with high efficiency, and its transgene expression is limited by the host's cellular immunity. The high prevalence of anti-adenovirus antibodies in the general population was thought to preclude adenovirus-mediated gene therapy. However, it was shown that local injection of rADV in pre-sensitized hosts results in levels of transgene expression at the injection site comparable to that of native animals (Bramson, et al., *Gene Ther* 1997; 4:1069-76). These findings stress both the applicability of this local gene and the potential for repeated treatments, if required. Although, for effective gene therapy, the transgene may need to be expressed in a higher percentage of cells in the target population, lower rates of expression may be sufficient if the gene product exerts a paracrine effect on neighboring cells. Toxicity to tissues other than the target, due to the broad tropism of the adenovirus, is usually seen only with systemic administration.

Adenoviruses can transduce both dividing and nondividing cells and the viral genome, remains episomal and does not integrate into host chromosomes. They can infect a broad range of human cells such as those in skin, lung, liver, brain, and blood vessels. It has recently been shown that adenoviral vectors are very effective for in vivo gene transfer to porcine and other experimental skin wounds and nearly microgram quantities of therapeutic protein can be expressed in the wound microenvironment (Liechty, et al., *Wound Rep Reg* 1999; 7:148-53; Liechty, et al., *J Invest Dermatol* 1999; 113: 375-83).

The usefulness of administration of ADV-VEGF in reducing the time needed for wound healing, as described in U.S. Ser. No. 60/363,584 filed Mar. 12, 2002, was recently confirmed in experimentally-induced excision wounds in diabetic mice (Romano Di Peppe, et al *Gene Therapy,* 9: 1271-1277 (October 2002)). A statistically significant reduction in wound healing time as compared to untreated mice was noted as early as 3 days after treatment, in mice treated with $10^8$ p.f.u. of AdCMV.VEGF$_{165}$ directly on the wound, There was also an increase in VEGF expression in the wounded skin and significant angiogenic response. The concentration of AD-VEGF can be titrated accordingly to result in expression of an effective amount of VEGF.

Polymeric Matrices

Alternatively, the VEGF is delivered using a sustained release device. Both non-biodegradable and biodegradable matrices can be used for delivery of genes, although biodegradable matrices are preferred. These may be natural or synthetic polymers, although synthetic polymers are preferred due to the better characterization of degradation and release profiles. The polymer is selected based on the period over which release is desired, generally in the range of at least two to six weeks, although longer periods may be desirable. In some cases linear release may be most useful, although in others a pulse release or "bulk release" may provided more effective results. The polymer may be in the form of a hydrogel (typically in absorbing up to about 90% by weight of water), and can optionally be crosslinked with multivalent ions or polymers.

High molecular weight genes can be delivered partially by diffusion but mainly by degradation of the polymeric system. In this case, biodegradable polymers, bioerodible hydrogels, and protein delivery systems are particularly preferred. Examples of non-biodegradable polymers include ethylene vinyl acetate, poly(meth)acrylic acid, polyamides, copolymers and mixtures thereof Examples of biodegradable polymers include synthetic polymers such as hydroxyacid polymers, for example, polymers of lactic acid and glycolic acid, polyanhydrides, poly(ortho)esters, polyurethanes, poly(butic acid), poly(valeric acid), and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the an), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In the preferred embodiment, the polymeric matrix is a microparticle between nanometers and one millimeter in diameter, more preferably between 0.5 and 100 microns for administration via injection. The microparticles can be microspheres, where the gene is dispersed within a solid polymeric matrix, or microcapsules, where the core is of a different material than the polymeric shell, and the gene is dispersed or suspended in the core, which may be liquid or solid in nature. Unless specifically defined herein, microparticles, microspheres, and microcapsules are used interchangeably.

Alternatively, the polymer may be cast as a thin slab or film, ranging from nanometers to four centimeters, a powder produced by grinding or other standard techniques, or even a gel such as a hydrogel. The polymer can also be in the form of a coating or part of a stent or catheter, vascular graft, or other prosthetic device.

The matrices can be formed by solvent evaporation, spray drying, solvent extraction and other methods known to those skilled in the art.

The release of VEGF from fibrin-based biomaterials was demonstrated by Wong et al., *Thromb Haemost* 89(3):573-82 March 2003). Fibrin-based biomaterial preparations can be used as provisional growth matrices for cells important in tissue repair during wound healing in vivo. VEGF was incorporated into the fibrin biomaterials prior to formation of the Fibrin Sealant clots. Clotting resulted in sustained release of VEGF causing angiogenic activity.

Prolonged controlled release has been achieved using several different devices. Examples include mini-implantable pumps for a variety of drugs especially chemotherapeutics and highly potent neuroactive drugs, silicon tubing with release controlling pores in the ends for birth control agents, and co-axial implants. Currently approved infusion procedures generally use an externally-worn or implanted pump. DUROS® sufentanil, an osmotic pump designed for 100-day delivery of sufentanil, is currently undergoing clinical testing. This implant is much smaller and easier to administer, and is described in WO 00/54745.

Effective Dosages of VEGF

Unlike in the case of an ischemic ulcer, for a diabetic ulcer, the challenge remains to keep a steady rate of angiogenic stimulation with minimal toxicity. At this stage in the field of wound healing, it appears that diabetic wounds have impaired angiogenesis. VEGF administered locally into the wound is the safest and most effective method to stimulate angiogenesis and to facilitate healing the diabetic wound.

The use of $VEGF_{165}$ has been established in multiple models of angiogenesis (Kaner, et al., *Am J Respir Cell Mol Biol.* 2000; 6:640-641; Muhlhauser, et al., *Circ Res.* 1995; 6:1077-1086) Human $VEGF_{165}$ molecule (rather than the murine molecule) has already been established in the preclinical studies for cardiac ischemia (using a porcine model, Esakof el al., *Hum Gene Ther.* 1999; 10:2307-2314; Lopez, et al., *Cardiovasc Res.* 1998; 40:272-281; Baumgartner, et al., *Annu Rev Physiol.* 2001; 63:427-450; Losordo, et al., *Am Heart J.* 1999; 138:132-141; Pearlman, et al., *Nat Med.* 1995; 1:1085-1089; Hariawala, et al., *J Surg Res.* 1996; 63:77-82), and a dog model (Banai, et al., *Circulation.* 1994; 89:2183-2189; Lazarous, et al., *Cardiovasc Res.* 1999:44; 294-302) which led to its eventual use and demonstrated efficacy in humans (Esakof, et al., *Hum Gene Ther.* 1999; 10:2307-2314; Sumes, et al., *Ann Thorac Surg* 1999; 68:830-7; Losordo, et al., *Circulation.* 1998; 98:2800-2804; Baumgartner, et al., *Am Heart J.* 1999; 138-132-41; Hendel, et al., *Circulation.* 2000; 101:118-121; Hammond, et al., *Cardiovasc Res.* 2001; 49:561-567; Sylven, et al., *Coron Artery Dis.* 2001; 12:239-243; Tio, et al., *Human Gene Therapy.* 1999; 10:2953-2960; Laitinen, et al., *Hum Gene Ther.* 2000; 11:263-270; Vale, et al., *Circulation.* 2000; 102:965-974).

Similarly, $VEGF_{165}$ was used in preclinical studies for limb ischemia and atherosclerosis in rabbits (Gennaro et al., *Circulation* Jan. 21, 2003; 107(2):230-3; Takeshita, et al., *Biochem Biophys Res Commun.* 1996; 227:628-635; Tsurumi, et al., *Circulation.* 1996; 94:3281-3290; Takeshita, et al., *J Clin Invest.* 1994; 93:662-670; Bauters, et al., *Circulation.* 1995; 91:2802-2809; Bauters, et al.,*J Vasc Surg.* 1995; 21:314-325; Takeshita, et al., *Circulation.* 1994; 90(suppl1II)):II-228-234; Vincent, *Circulation.* 2000; 102:2255-2261) and diabetic mice, which led to its eventual clinical trial testing and demonstrated efficacy for patients (Simovic, et al., *Arch Neurol.* 2001; 58:761-768; Isner, et al., *J Vasc Surg.* 1998; 28:964-75). Recently, human VEGF has been used in diabetes (e.g., for diabetic neuropathy in rats, (Samii, et al., *Neurosci Lett.* 1999; 262:159-162; Schratzberger, et al., *J Clin Invest.* 2001; 107:1083-1092) for diabetes-related impairment of angiogenesis in mice, (Rivard, et al., *Am J Pathol.* 1999; 154:355-363) for ischemic neuropathy in rabbits, (Schratzberger, et al., *Nat Med.* 2000; 4:405-413) and in patients (Baumgartner, et al., *Circulation.* 1998; 97:1114-1123; Isner, et al., *Hum Gene Ther.* 1996; 7:959-988; Isner, et al., *Lancet.* 1996; 10:370-374; Schratzberger, et al., *J Clin Invest.* 2001; 107:1083-1092). Furthermore, successful treatment of diabetic neuropathy in rodents led to human trials for efficacy of chronic ischemic neuropathy in patients (Simovic, et al.,*Arch Neurol.* 2001; 58:761-768). A vast amount of literature has demonstrated that the use of human VEGF in a mouse shows functionality due to a high degree of homology between the two species-specific proteins (90%, data from BLAST® protein homology searching). Finally, according to the European Molecular Biology Laboratory (EMBL) database, the amino acid of human VEGF protein and murine VEGF proteins demonstrate only one amino acid difference (215 vs. 214).

An effective dosage can be determined by extrapolation based on animal studies, for example, using a mouse model. In previous local therapy studies, the use of full thickness excisional wounds in diabetic mice has been shown to be useful for developing therapies for eventual use in patients. The mouse model has been successful in bringing growth factor therapy from the lab to the bedside. Both FDA approved drugs that are currently efficacious for diabetic ulcers (PDGF-BB and human skin equivalent) utilized the murine model in the vast majority of their preclinical testing.

The C57BL/KsJ db/db mouse is a particularly useful model since it has been shown to have decreased angiogenesis (Altavilla, et al., *Diabetes.* 2001; 50:667-673; Coleman, *Diabetes.* 1982; 31 (Suppl: 1 Pt 2):1-6). Tissue repair in C57BL/KsJ db/db mice has proven to be a clinically relevant model of impaired wound healing. The animals exhibit several characteristics of adult onset diabetes, including obesity, insulin-resistant hyperglycemia and markedly delayed wound closure.

C57BL/KsJ-db/db mice, homozygous for the diabetes spontaneous mutation, become identifiably obese around 3 to 4 weeks of age. Elevations of plasma insulin begin at 10 to 14 days and of blood sugar at 4 to 8 weeks. Homozygous mutant mice are polyphagic, polydipsic, and polyuric. The course of the disease is markedly influenced by genetic background. A number of features are observed on the C57BL/KsJ db/db background, including an uncontrolled rise in blood sugar, severe depletion of the insulin-producing beta-cells of the pancreatic islets, and death by 10 months of age. Exogenous insulin fails to control blood glucose levels and gluconeogenic enzyme activity increases. The diabetic mutation is a result of a point mutation in the leptin receptor gene, lepr. This point mutation promotes abnormal splicing creating a stop codon that shortens the intracellular domain of the receptor, so that its signaling capacity is curtailed. The ligand, Leptin, has been shown to be a key weight control hormone that takes a mutant form in the mouse obesity mutation, Lepob (JAX Mice database: http://jaxmicejax.org/jaxmice-cgi/jaxmiced-b.cgi).

C57BL/KsJ-db/db mice exhibit characteristics similar to those of human adult onset diabetes (NIDDM Type II) as a result of a single autosomal recessive mutation on chromosome 4. Only the homozygous animals develop diabetes, This strain also expresses lower levels of several growth factors and receptors, accounting, at least in part, for the reduced rate of healing (Werner, et al., *J Invest Dermatol* 1994; 103:469-473).

The streptozotocin diabetic mouse is another model for studying the pathology of diabetes. Mice are rendered diabetic by intraperitoneal injection of streptozotocin administered for five consecutive days. Streptozotocin-treated mice become hyperglycemic and also show impaired wound healing when compared to healthy animals (Matsuda et al. *J Exp Med* 1998; 187:297-306; Brown et al *Am J Pathol* 1997; 151:715-724). The streptozotocin-induced diabetic mouse has been widely studied and is known to those of skill in the art.

The diabetic mouse model (Geerlings et al., *FEMS Immunol Med Microbiol.* 1999; 3-4:259-265; Feige, et al., *EXS.* 1996; 77:359-373; Bessman, *J Diabetes Complications.* 1992; 4:258-262; Abraham, et al., *J Dermatol.* 1990; 7440-447; Loots, et al., *J Invest Dermatol.* 1998; 5:850-857; Brown, et al., *J Surg Research* 1994; 56:562-570; Greenhalgh, et al., *Am J Pathol* 1990; 136:1235-1246; Tsuboi, et al., *J Explorer Med* 1990; 172:245-251; Matuxzewska, et al., *Pharm Res* 1994; 11:65-71; Darby, et al., *Int J Biochem Cell Biol* 1997; 29:191-200; Livant, et al., *J Clin Invest.* 2000; 105:1537-1545; Yamamota, et al., *Europ J Pharm* 1996; 302: 53-60; Wetzler, et al., *J Invest Dermatol.* 2000; 115:245-253; Sun, et al., *J Invest Dermatol* 1997; 108:313-318; Sun, et al., *J Invest Dermatol.* 1996; 106:232-237; Zykova, et al., *Diabetes.* 2000; 49:1461-1458; Beer, et al., *J Invest Dermatol.* 1997; 109:132-138) has been widely accepted in the study of therapeutic agents that may be effective in the treatment of chronic wounds, it has been successfully used in preclinical testing for other growth factor therapies, and it offers a good model for patients with diabetic foot ulcers.

The present invention will be further understood by reference to the following non-limiting examples.

Example 1

Non Diabetic Wounds are Angiogenic Dependent and Have Delayed Contraction with Angiogenic Inhibitors There are multiple stimuli for angiogenesis in the first few hours after a wound is created, but it is usually 3 days before new vessel formation can be visualized histologically in the wound. Throughout the wound healing process, angiogenesis maintains a critical role in the healing response (Brem, et al., *Bone Formation and Repair American Academy of Orthopedic Surgeons*/Rosemont, Ill., 1994. pp 213-222; Arbiser. *J Am Acad Dermatol* 1996; 34:486-497; Pettet G, et al., *Proc R. Soc Lond* 1996; 263: 1487-1493; Arnold, et al., *Pharmacol Ther* 1991; 52:407-422; Seifert, et al., *Explorer Mol Pathol* 1997; 64:31-40; Folkman, *Growth Factors: From Genes to Clinical Application.* Karolinska Institute Nobel Conference Series. New York, N.Y., Raven Press, 1990, pp 201-216; Folkman, et al., *Inflammation: Basic Principles and Clinical Correlates*, ed 2. New York, N.Y., Raven Press, 1992, pp 821-839; Hunt, et al., *Surgery* 1984; 96:48-54).

Angiogenesis occurs in a time-dependent manner in relation to the wound healing process. For example, when a potent angiogenic inhibitor (e.g., TNP-470, also known as AGM-1470) is given systemically, wound closure and breaking strength are significantly decreased in a time-dependent manner. If the angiogenesis inhibitor is given before or 5 days after wound creation, there is no delay in wound closure, but if it is given in the first 5 days after wounding a sharp delay in closure is noted.

These experiments demonstrate the importance of the initiation of angiogenesis in contributing to the multiple processes in normal wound healing, such as wound closure and breaking strength. In the healing of acute wounds, these results show that the angiogenic response is time-dependent. This experiment establishes that decreased angiogenesis delays wound closure. In chronic wounds, such as diabetic ulcers, the angiogenic response is impaired as long as the wound is present, secondary to multiple etiologies.

Example 2

The Viral Vector

The human cDNA for VEGF was cloned into a recombinant adenovirus vector. Human umbilical vein endothelial cells (HUVEC) were harvested from fresh umbilical cords using a 0.2% collagenase solution in Hanks Balanced Salt Solution (HBSS) for 20 minutes at room temperature. The cells were washed with HBSS and plated on collagen-coated (1% in PBS) tissue culture dishes in M13 medium supplemented with 20% FBS and 1 mg/ml of bFGF, HUVEC from a confluent 10-cm plate were homogenized and total RNA was extracted with the RNEASY™ kit from QIAGEN® Inc. First strand of cDNA was amplified from the RNA by RT-PCR with oligo-dT primers using the SUPERSCRIPT™ II RT PCR kit from LIFE TECHNOLOGIES®. The full-length human VEGF cDNA was then amplified by PCR with appropriate primers (sense 5'-CCCAAGCTTGCCGCCGCCAT-GAACTTTC TGCTGTCT-3' (SEQ ID NO:1); Hind III linker antisense, 5'-GCTCTAGAATCTGGTTCCCGAAAC-CCTGA-3' (SEQ ID NO:2), Xba I linker) using pfu (plaque forming units), DNA polymerase (STRATAGENE®). The product corresponding to the size of $VEGF_{165}$ was gel-purified and cloned into pBluescript (STRATAGENE®), to be spliced between the Hind III and Xba I sites. After confirmation by automatic sequencing, the $hVEGF_{165}$ cDNA was cloned into the ADV shuttle vector pADV RSV-bPA downstream of the RSV LTR. The ADV shuttle vector was then co-transfected with the adenovirus type 5 genome containing backbone vector pBHG100 into 293 cells (E1 positive packaging cell line) by standard calcium phosphate precipitation, The ensuing viral plaques were isolated and in vitro screened for transgene expression and functional activity of the transgene. A positive plaque (#11-1) was then selected and expanded. The virus ($ADV.hVEGF_{165}$) was released from the producer cells by three freeze/thaw cycles and purified over a CsCl gradient. The viral particles were measured by spectrophotometric analysis ($OD_{260}$) and the plaque-forming units (pfu) were determined by standard agarose overlay plaque assay on 293 cells.

The vector, as constructed, resulted in gene transfer, ascertaining transgene expression in target cells in culture. JC cells, a VEGF-negative murine breast cancer cell line which is easily transducible by adenovirus, were infected with virus of different plaques of $ADV.hVEGF_{165}$ or ADV.beta Gal (negative control) with an MOI of 100. VEGF was measured after 48 hours in the conditioned supernatant by hVEGF ELISA (R&D Systems), according to the manufacturer's instructions. The ELISA results for hVEGF of conditioned supernatant of JC cells transduced are:

1) Virus of different plaques of ADV.hVEGF$_{165}$: (plaques 11-1; 11-2; 11-3; 11-9; 13-1; 16-1);
2) Control vector (beta-Gal); and supernatant of uninfected JC cells. (VEGF standard curve with recombinant VEGF protein supplied by the manufacturer).

The transgene for VEGF stimulates endothelial cell proliferation in vitro. The function of the transgene was assessed through induction of HUVEC proliferation by conditioned supernatant of ADV.hVEGF$_{165}$ or ADV beta Gal transduced JC cells, respectively. HUVECs were seeded in flat-bottom well plates pre-coated with 1% gelatin (in PBS) at 2×10$^3$ cells/well and serum-starved overnight (M13 medium without FBS). Conditioned supernatant was then added in several dilutions and cells were cultured for an additional 48 hours in M13 supplemented with 20% FBS, but no growth factors. HUVEC proliferation was measured by a tetrazolium-based assay at an absorption of 450 nm according to the manufacturer's instructions, EZ4U™ kit by Biomedica. Measurements of HUVEC proliferation by a tetrazolium-based assay after a 48-hour stimulation with log 2 dilution of conditioned supernatant of JC cells were transduced with:
1) virus of different plaques of ADV.hVEGF$_{165}$: (plaques 11-1, 13-1, 16-1); and
2) control vector (b-Gal).

Addition of recombinant VEGF protein (Pepro Tech Inc.) to the culture medium in a log 2 dilution series from 100 ng/ml to <1 ng/ml was used as a positive control.

The results are shown in FIG. 1.

Example 3

ADV-VEGF Leads to Angiogenesis

Mice received subcutaneous injections of ADV-VEGF in one thigh and ADV.LacZ in the other. At various time intervals, these mice were sacrificed and perfusion-fixed. The thighs were harvested and processed for histology and immunohistochemistry. Histology revealed no significant changes in the control (ADV.LacZ)P group and marked presence of new blood vessels in the ADV-VEGF group.

Thus, it was established that ADV-VEGF infected cells secreted human VEGF$_{165}$ and that this protein product stimulated endothelial cell proliferation in vitro and angiogenesis in vivo, without local necrosis.

Examples 4-7 use a mouse model. For all mouse wound experiments, mice were purchased from Jackson Laboratories, and housed one per cage. Animals were anesthetized in a chamber in preparation for all experiments and shaved the day before experimentation. Full thickness wounds were made with a template of 0.8 or 1.4 cm in diameter. All wounds were created in exactly the same location, 15 mm from the last cervical vertebra on the mouse dorsum. The marked area was excised with scissors to include the epidermis, dermis, and panniculus carnosus. The wounds were then photographed on the day of wounding. The photographs and digital images were taken with a NIKON® 35 mm camera and a NIKON® digital camera, respectively, at a fixed distance from the wound. A photo ruler was placed in the field of the photograph and labeled with the mouse's identification number and date. Digital photos were used to assess length and width measurements and the area was calculated from planimetry. Length and width were also recorded in the lab notebook at the time of photography. The data included in these studies are maintained in a database, created with MICROSOFT ACCESS®, on a DELL™ Dimension XPS R450 Computer, and backed up on an IOMEGA® Jaz Drive. Both film and digital photographs of each mouse were printed within 7 days of being taken and kept in a secure area. The digital images were measured using Med-Data Systems' Wound Imager program. An identical data system is utilized to follow clinical patients treated for diabetic foot ulcers. In all experiments, the ADV-VEGF was injected into 4 quadrants of the dermis of the newly created wound edge utilizing a Hamilton™ microliter syringe in 4 equal volumes.

This model is analogous to clinical situations where patients are routinely treated for diabetic foot ulcers, where the wound is debrided prior to initiation of growth factor therapy (PDGF-BAL) or cell therapy (human skin equivalent comprising cultured keratinocytes and fibroblasts on type I collagen). The emphasis is on converting a chronic wound or ulcer into an acute wound, in part, by debridement of tissue, leaving fresh wound edges. This approach is a standard of care and is the basis of the experimental design, allowing for the maximally effective injection of VEGF into the sharply excised wound edges.

Example 4

Effect of ADV-VEGF

The dosage of 5×10$^{11}$ viral particles (VPs) of ADV-VEGF was used because this was the maximal amount of viral particles that could be placed in a limited volume (up to 400 µl, which is the maximum that can be administered without the volume affecting the wound). This dosage was also based on multiple other preclinical and clinical trials performed at our institution, which determined this to be safe for ADV particles. It has become clear that the total load of ADV particles contributes to toxicity. Therefore, the FDA has requested that experiments use viral particles rather than pfus. Pfu is a biological assay measuring activity of the virus, which can vary by up to one log using the same batch of virus in different assays. If different batches of virus are used, there may be a significant variation in particle measurements. To prevent this potential problem from occurring and to keep the loads constant, the same batch of virus was used for all experiments.

Six groups, comprising 5 mice each, were used. Wounds of 0.8 cm were made with a template, as described above. All, except group F, used the C57BL/KsJ-db/db mouse model.
Group A: (ADV-VEGF) received 5×10$^{11}$ ADV-VEGF VPs at the time of wounding. The wounds closed on average in 13.6± days.
Group B: (ADV-DL312, control null vector) received 5×10$^{11}$ VPs at the time of wounding. The wounds closed in 26.9±0.4 days.
Group C: (saline control) received PBS and their wounds closed in 26 days, on average.
Group D: (2$^{nd}$ injection of ADV-VEGF) received a second injection of ADV-VEGF 7 days after wounding. The results were not statistically different from Group A.
Group E: (human recombinant VEGF) received 2.5 µg recombinant VEGF at the time of wounding. The wounds closed at a rate similar to Groups B and C.
Group F: (wild type, non-diabetic mice) received saline. The wounds closed in 12 days, on average.

The results show that treatment with ADV-VEGF resulted in a (highly) significant reduction in time to closure of wounds in diabetic mice (p<0.01, Student's t-test and non-parametric Mann-Whitney/Wilcoxon's test). Although these results suggested that a single treatment with ADV-VEGF was maximally effective in accelerating wound closure, the study was limited.

Example 5

Dose-Response Study

Despite the limitations of the above experiment and the small number of mice, the promising results motivated determining if a lower dose may be effective. In order to determine if gene therapy is effective, it is first necessary to perform a dose-response experiment. This allows one to establish that there is a causal relationship between the therapy and its therapeutic effects. It was found that in these small 0.8 cm wounds $5\times10^{10}$ and $5\times10^{11}$ VPs of ADV-VEGF both significantly accelerated the closure of diabetic ulcers in db/db male mice, as compared to $1.6\times10^{10}$ ADV-VEGF VPs and PBS.

There was a significantly ($p<0.05$) greater improvement in the rate of healing for the high dose group, compared to the control group.

A limitation in this experimental design was that the occlusive dressing placed on the wound after each photograph was taken resulted in broad contamination with culture-proven gross purulence with *Pseudomonas aeruginosa*. The technique was modified to utilize only a clear occlusive dressing during the first 5 days after the wound was made. No infection has been seen in subsequent experiments. However, this provided a serendipitous and important finding. This experiment suggests that ADV-VEGF may reverse bacterial contamination of a wound. This is particularly important, because almost all patients with diabetic foot ulcers have some degree of infection or, more specifically, bacterial contamination, which is the single greatest contributing factor to the morbidity and mortality related to these wounds.

Example 6

Effect of VEGF on Larger Wounds

Example 5 established that even a lower dose of gene therapy might be effective. However, these experiments were limited by the occurrence of infection and the small number of groups. The next experiment determined whether a single high dose of ADV-VEGF would be effective in larger wounds.

This experiment tested the hypothesis that ADV-VEGF will be effective in accelerating wound closure, even when the size of the wound is increased, with metabolic control ascertained (therefore female mice were utilized). Since patients usually present with larger wounds, the size of the wound was doubled to 1.4 cm which represents 35% of the total diameter of the mouse dorsum. Four treatment groups at 0.5 log differences and two control groups were tested. One set of controls was injected with saline at the time of injection and the other with ADV-DL312 $5\times10^{11}$ particles/wound.

The only group showing a statistically significant acceleration of closure was the group treated with $5\times10^{11}$ VPs ADV-VEGF (which was the maximum dose tested). Therefore, it is necessary to determine if a greater acceleration of healing can be obtained. Another limitation of this experiment was that these mice were 12-14 weeks old, older mice exhibit poor metabolic control. The glucose levels in all groups were between 300-310. This is too high and may have affected the results, since this places the mice in a particularly catabolic state, which is not analogous to the clinical situation.

Example 7

Determination of Toxicity

10 Mice Per Group

A comprehensive examination was initiated to look for indicators of toxicity. The liver was examined for any signs of hepatitis. The lungs were examined because angiogenic therapy can potentially cause petechia in lungs and bleeding. The kidneys were examined at the histological level because nephropathy is very common in diabetics and could be precipitated by angiogenic therapy. The cecum was analyzed because it is the most rapidly proliferating organ in the body and any therapy that may effect a wound could also effect the rapidly dividing epithelium. The retina was examined closely because it is of great concern whether systemic therapy could cause retinopathy. In addition, the heart was analyzed because of concerns that angiogenic therapy could adversely effect this muscle. The brain was examined because it is known that angiogenic therapy can cause petechia and bleeds in the brain, which is particularly susceptible in the diabetic CNS vasculature.

There were no pathologic findings in any organs 90 days after $5\times10^{11}$ VPs of ADV-VEGF was administered into the diabetic ulcer. In the liver, there was neither acute hepatitis from the ADV nor proliferation of the sinusoidal lining of the endothelial cells from the VEGF. The kidneys, lungs, retina, or cecum had neither hemorrhage nor any other pathologic findings. Similarly, neither the heart or brain (not shown) had any abnormal pathologic findings. This is significant, because in past experience, angiogenic therapy was reported to have a significant effect on the immune system, however no gross difference in weight, size, or histological examination of the organs were manifested.

At this point, the experiment was limited, because only 3 time points were assayed and, at most, only 5 mice were tested at any time point. The consistency of the results suggests that they can be duplicated in significantly higher numbers. After 3 months a toxic effect may have been realized, but it was transient.

It was then determined whether VEGF levels in the serum of diabetic mice were increased after ADV-VEGF local administration. VEGF serum levels were determined by a commercially available ELISA kit in accordance with the manufacturer's protocol. It is emphasized that human VEGF was assayed in the serum. A linear VEGF standard curve was generated for each assay ($r=0.99$ to 1 between calculated and measured VEGF levels) with the supplied recombinant VEGF protein in the range from 10000 pg/ml to 15.6 pb/ml and serum levels were calculated accordingly. Only 3-5 mice per group were studied, enough to determine that the assay was accurate and consistent. VEGF levels demonstrated a peak of activity in day 10 after the wound was made. However, there were no differences in the control group treated with saline versus the ADV-VEGF group.

Utilizing the same series of mice, larger quantifies were studied ($5\times10^{11}$ vp of ADV-VEGF and $5\times10^{11}$ vp of ADV-DL312 vs. PBS, respectively) and the effects on the organ weights of the lungs, kidneys, and spleen measured. No differences were found for tested time points. However, the sampling size is too small to draw any definitive conclusions. Preliminary data from days 5, 10, 15 and 90 $5\times10^{11}$ ADV-VEGF, $5\times10^{11}$ ADV-DL$^{312}$ vs. PBS, respectively) of serum chemistries: ALT, AST, ALP, Bilirubin, Creatinine, Glucose, BUN, Platelets, WBC, and Hemoglobin show no differences detected to date.

In summary, the preliminary data suggest that $5\times10^{11}$ Vp of ADV-VEGF accelerates ulcer healing in C57BL/KsJ-db/db mice. VEGF stimulates angiogenesis and accelerates the healing process as evidenced by:

1) a reduced time to closure (a healed wound is defined as 100% epithelialization and no drainage) in experimental diabetic ulcers, and
2) accelerated epithelialization and increased cellular density.

The preliminary data suggest that a high dose of $5\times10^{11}$ ADV-DL312 VPs/wound is effective. However, such a high dose of ADV particles unlikely to be utilized in patients in years to come because of concerns of potential toxicity.

Modifications and variations of the present invention will be obvious to those skilled in the art from the foregoing detailed description. Such modifications and variations are intended to come within the scope of the following claims.

I claim:

1. A method for enhancing the rate of repair of a diabetic ulcer comprising administering to the diabetic ulcer a nucleic acid molecules encoding VEGF, wherein an effective amount of VEGF is expressed over a sustained period of time of at least two weeks to enhance the rate of closure of the diabetic ulcer.

2. The method of claim 1 wherein the VEGF reverses bacterial contamination of the diabetic ulcer.

3. The method of claim 1 wherein the nucleic acid molecule is in the form of naked DNA encoding VEGF.

4. The method of claim 1 wherein the nucleic acid molecule is a viral vector.

5. The method of claim 4, wherein the viral vector is an adenoviral vector.

6. The method of claim 5 wherein the method comprises administering the adenoviral vector in an amount of at least $1.6 \times 10^{10}$ adenoviral-VEGF particles.

7. The method of claim 5 wherein the method comprises administering the adenoviral vector in an amount of at least $5 \times 10^{10}$ adenoviral-VEGF particles.

8. The method of claim 5 wherein the method comprises administering the adenoviral vector in an amount of at least $5 \times 10^{11}$ adenoviral-VEGF particles.

* * * * *

SEQUENCE LISTING

<160> NUMBER OF SEQ ID NOS: 2

<210> SEQ ID NO 1
<211> LENGTH: 36
<212> TYPE: DNA
<213> ORGANISM: Homo sapiens

<400> SEQUENCE: 1
cccaagcttg ccgccgccat gaactttctg ctgtct                            36

<210> SEQ ID NO 2
<211> LENGTH: 29
<212> TYPE: DNA
<213> ORGANISM: Homo sapiens

<400> SEQUENCE: 2
gctctagaat ctggttcccg aaaccctga                                    29